United States Patent [19]
Albert

[11] 4,259,582
[45] Mar. 31, 1981

[54] PLURAL IMAGE SIGNAL SYSTEM FOR SCANNING X-RAY APPARATUS

[76] Inventor: Richard D. Albert, 317 Hartford Rd., Danville, Calif. 94526

[21] Appl. No.: 90,540

[22] Filed: Nov. 2, 1979

[51] Int. Cl.³ .................. H05G 1/00; H05G 1/30; G01T 1/00; H04N 5/32
[52] U.S. Cl. .................... 250/402; 250/355; 250/416 TV; 358/111
[58] Field of Search ............ 250/416 TV, 402, 408, 250/409, 355; 358/111, 166, 169

[56] References Cited

U.S. PATENT DOCUMENTS

| | | | |
|---|---|---|---|
| 2,837,657 | 6/1958 | Craig et al. | 250/416 TV |
| 3,567,854 | 3/1971 | Tschautz | 250/416 TV |
| 3,949,229 | 4/1976 | Albert | 250/402 |
| 4,032,784 | 6/1977 | Rich | 250/355 |
| 4,032,787 | 6/1977 | Albert | 250/402 |
| 4,144,457 | 3/1979 | Albert | 250/416 TV |
| 4,149,076 | 4/1979 | Albert | 250/402 |

Primary Examiner—Alfred E. Smith
Assistant Examiner—Carolyn E. Fields
Attorney, Agent, or Firm—Phillips, Moore, Weissenberger, Lempio & Majestic

[57] ABSTRACT

Radiographic images are produced by situating a subject (13) between a scanning x-ray source (16) and an x-ray detector (14) to produce electrical signals indicative of variations of x-ray transmissivity in different regions of the subject (13). A signal processing system (11) enables simultaneous display of a plurality of visible images at a plurality of display devices (52 to 55) with each image emphasizing a different aspect of the information generated by a given scanning of the subject. A feedback circuit (68) from the detector (14) to the x-ray source (16) maintains the average level of the detector signal constant while allowing short term fluctuations so that only abrupt or brief changes of x-ray transmissivity in the subject are visible in a first image at a first display device (52). A second image signal circuit (93) recovers the data suppressed by the feedback circuit (68) to enable a full contrast range image to be presented at another display device (53) and to enable display at additional display devices (54, 55) of still more images, each of which emphasizes a different selected contrast range from the total range of subject transmissivity variations developed by the scanning of the subject (13). Radiation exposure of the subject (13) is reduced by enabling extraction and display of a greater amount of information from a given scanning of the subject (13).

15 Claims, 5 Drawing Figures

FIG-1

PLURAL IMAGE SIGNAL SYSTEM FOR SCANNING X-RAY APPARATUS

TECHNICAL FIELD

This invention relates to radiography and more particularly to the processing of image signals produced by a scanning x-ray system in which a subject to be imaged is situated between an x-ray detector and an x-ray source that produces a moving x-ray origin point.

BACKGROUND OF THE INVENTION

Conventional radiographic procedures, in which x-rays from a fixed origin point pass through a subject to a broad photographic film or florescent screen, have serious limitations and disadvantages. Only a small proportion of the x-rays which reach the film or screen cause an actinic or florescent reaction. Consequently, an undesirably high radiation dosage of the subject, which may be a medical or dental patient for example, is necessary to obtain the desired data. Where film is employed, the image is not immediately available as the developing process requires time and specialized equipment.

Further, both photographic film and florescent screens have a very limited contrast range or gray scale capability in comparison with the full range of x-ray transmissivity variations between different regions of many subjects. Consequently, the full range of information which is potentially available from a given exposure of a subject is not visible or detectable in the film or screen. An exposure of a medical patient may, for example, be arranged to produce a film or florescent screen radiograph depicting dense bone structure. Owing to the limited contrast range of the film or screen, it is not possible to perceive, in the same image, a region of soft tissue such as a tumor that has an x-ray transmissivity differing only slightly from the adjacent soft tissue. If the exposure is adjusted to depict contrast differences between regions of soft tissue, than details of the relatively radiopaque bone structures are not present in the image. Consequently, repeated exposures of the subject may be necessary to obtain all of the information which may be needed. This further increases the radiation dosage of the subject.

These problems can be greatly alleviated by utilizing scanning x-ray apparatus for producing radiographic image data, an example of such apparatus being described in U.S. Pat. No. 3,949,229 issued Apr. 6, 1976 to Richard D. Albert for X-RAY SCANNING METHOD AND APPARATUS. In a scanning system of this kind the subject is situated between an x-ray source which generates a moving x-ray origin point, in response to raster sweep signals, and at least one relatively small x-ray detector. The detector produces signals that vary in accordance with variations of x-ray transmissivity within the subject. An X-Y display device, such as a cathode ray tube oscilloscope or a television receiver, may be provided with sweep signals corresponding to those of the x-ray source while the Z or intensity signal for the display device is derived from the x-ray detector signals. A radiographic image of the scanned region of the subject is then produced at the screen of the display device.

The scanning x-ray apparatus can produce instantaneous images and greatly reduces radiation dosage of the subject since electronic x-ray detectors respond to a much larger proportion of intercepted x-rays than film or florescent screens.

Further, the scanning system enables extraction and display of a much greater range of information from a single exposure of the subject. Although the display screens of cathode ray tubes or the like also have a very limited contrast or gray scale range in relation to the full range of x-ray transmissivity variations encountered in the scanning of many subjects, the x-ray detector signals may be transmitted to a plurality of such display means with each being adjusted to image a different limited contrast range selected from the full range of contrast information present in the detector signals. U.S. Pat. No. 4,032,787 issued June 28, 1977 to Richard D. Albert and entitled METHOD AND APPARATUS PRODUCING PLURAL IMAGES OF DIFFERENT CONTRAST RANGE BY X-RAY SCANNING discloses one form of signal processing circuit with which detector signals from a single exposure of a subject may be used to simultaneously display a plurality of images each of which depicts a different selected range of x-ray transmissivity variations within the scanned region of the subject.

Scanning x-ray systems also enable processing of the detector signals to impart advantageous characteristics to the radiographic images. As described in the above identified U.S. Pat. No. 3,949,229, with particular reference to FIG. 13 thereof, a feedback signal circuit may be provided between the x-ray detector and x-ray source which varies the production of x-rays at the source in such a manner that the average level of the detector signals is maintained substantially constant while regions of the subject that may have greatly different x-ray transmissivities are scanned. This suppresses certain data from the detector signal in order to emphasize other desired data. More specifically, the detector signal then varies only in response to scanning across abrupt boundaries between regions of the subject having different x-ray transmissivities. Changes of transmissivity which occur relatively gradually in the course of the scan and sustained changes are not represented in the detector signal. The result is a highly advantageous edge enhancement effect which makes the outlines of regions of the subject of differing transmissivity readily apparent in the image. Regions which may have only slightly differing transmissivities are readily apparent as it is primarily the abruptness of a transmissivity change rather than the magnitude of the change that varies the detector signal.

The advantageous effects of the feedback circuit are gained at the cost of suppressing information, which would otherwise be available, from the output of the x-ray detector. The feedback circuit may eliminate, from the detector signal, a very large amount of contrast or transmissivity variation data pertaining to the scanned region of the subject. Thus, using known systems, it is not possible to produce specialized images such as the edge enhanced image discussed above while also producing from the same radiation exposure of the subject certain other highly useful images such as plural images of different contrast range selected from the total range of contrasts present in the scanned region of the subject.

Thus, using known systems for processing signals from scanning x-ray apparatus, the obtaining of certain kinds of desirable image information has the effect of interfering with obtaining of other kinds of useful image information from the same exposure of the subject. To minimize radiation dosage and to enable the extraction of a greater variety of useful image information from a given scanning of the subject, it is preferable that signal processing means be available for simultaneously generating plural image signals of different informational content including image signals indicative of data which has been suppressed from the output of the x-ray detector in the process of producing others of the image signals.

The scanning x-ray systems discussed above are of a type primarily used for producing shadowgraph images. Essentially similar problems can be encountered in certain other types of x-ray scanning system such as computed axial tomograph x-ray scanners of the type which produce an essentially cross-sectional image of the scanned subject.

DISCLOSURE OF INVENTION

The present invention is directed to overcoming one or more of the problems as set forth above.

In one aspect of this invention a signal processing system is provided for a scanning x-ray apparatus of the type which has an x-ray source producing a moving x-ray origin point and which has at least one x-ray detector for disposition at the opposite side of the subject to be scanned to produce detector signals from which radiographic images of the subject may be derived. The system include means for generating a feedback signal which regulates the x-ray source to maintain the average value of the detector signals substantially constant while enabling the detector signals to vary briefly in response to scanning across boundaries between regions of the subject which have different x-ray transmissivities. To provide for the display of a plurality of images, each of which may emphasize a different aspect of the subject, a first image signal circuit produces first image signals in response to the brief variations of the detector signals and a second image signal circuit produces second image signals containing a greater range of contrast information than the first image signals, the second image signal circuit having signal combining means for combining the feedback signals and the first image signals to produce the second image signals.

In another aspect of the invention, one or more third image signal circuits are provided, each having means for selecting and transmitting only a predetermined limited portion of the total range of signal variations present in the second image signals.

In another aspect of the invention, the system includes a plurality of display means for generating separate visible radiographic images in response to any or all of the first, second and third image signals and in response to sweep signals synchronized with those of the x-ray source.

In still another aspect of the invention, data storage means are provided for receiving and storing sets of the signals and for subsequently reproducing some or all of the first, second and third image signals for transmission to the display means.

A signal processing system embodying aspects of the invention reduces radiation dosage of the subject and simplifies radiographic procedures by enabling extraction and either immediate or deferred display of a greater variety of image information from a given radiation exposure of the subject.

During the scanning of the subject the system produces, simultaneously, a plurality of image signals, from which a plurality of images may be generated with each image emphasizing a different aspect of the scanned region of the subject. A feedback signal from the detector may be used to vary x-ray production at the scanning x-ray source to suppress sustained changes of the detector signal when the scan passes into a region of the subject having an x-ray transmissivity differing from that of the preceeding region. First image signals derived from the detector signals then exhibit an edge enhancement effect which emphasizes boundaries. Although this may eliminate much valuable contrast information from the detector output, such information is made available for one or more additional images through second image signals produced by combining the first image signals and the feedback signals. Still other images may be generated from the same scanning of the subject, each emphasizing x-ray transmissivity variations between regions of the subject of a different selected magnitude or contrast range. Third image signals for this purpose may be produced by selecting and amplifying only limited portions of the total range of variation of the second image signals.

In some embodiments of the invention, additional specialized images may be generated which identify the precise orientation of the subject relative to the x-ray source and detector. This facilitates positioning of the apparatus to image a desired portion of the subject and facilitates later duplication of the positioning to obtain comparative images.

Still other aspects and advantages of embodiments of the invention will be apparent from the following description.

BEST MODE OF PRACTICING THE INVENTION

Figure 1:
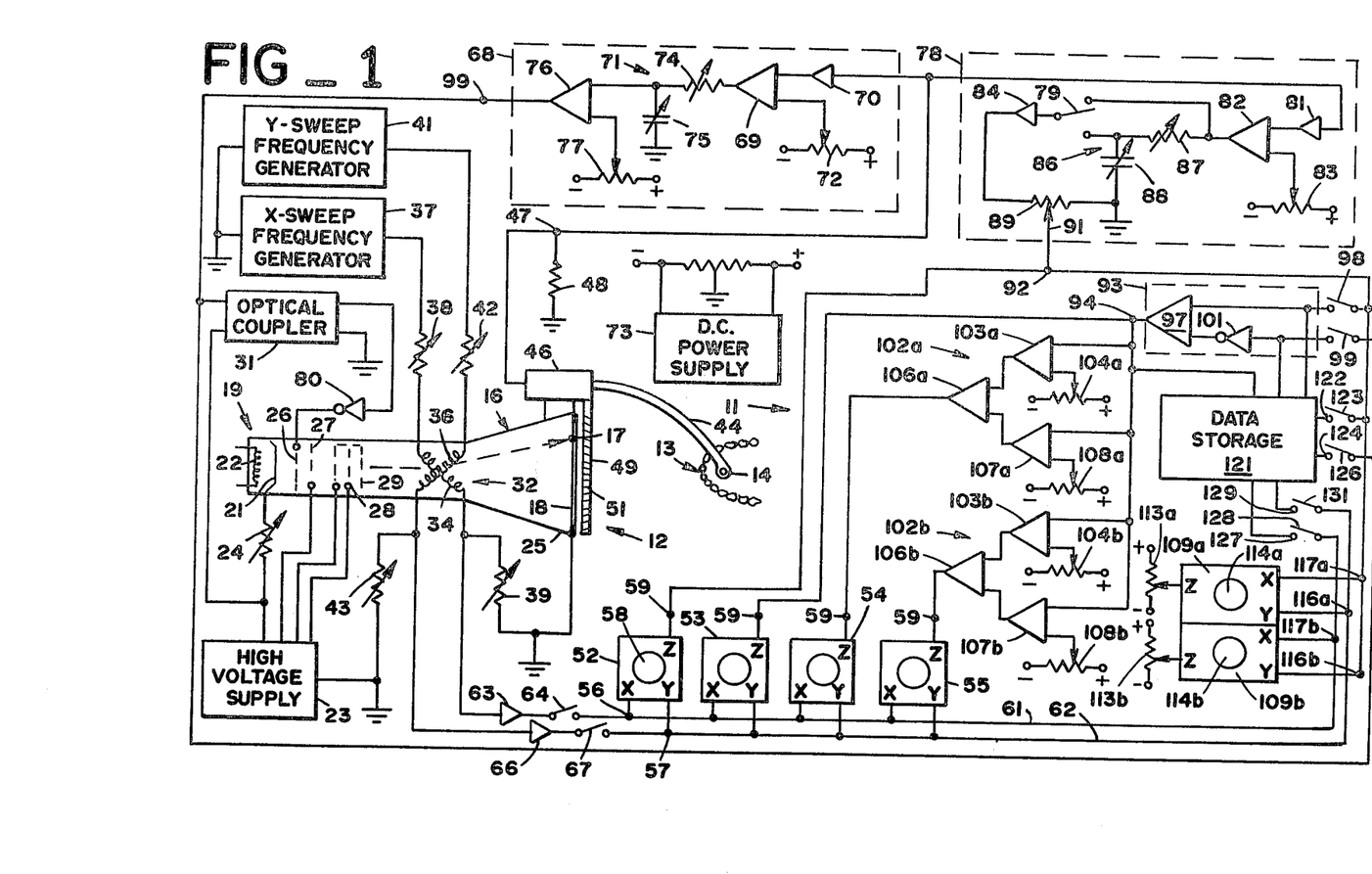
FIG. 1 is a schematic circuit diagram of scanning x-ray apparatus including an embodiment of the present invention.

Referring to FIG. 1 of the drawing, a signal processing system 11 is shown coupled to scanning x-ray apparatus 12 of the general type described in prior U.S. Pat. No. 3,949,229, hereinbefore more fully identified. Scanning x-ray apparatus 12 of this type generates electrical signals from which visible images of a subject 13 may be produced, the subject in this particular example being the lower front incisor teeth of a dental patient. While the invention will be herein described with reference to dental radiology for purposes of example, the apparatus may also be adapted for medical usage and for producing images of inanimate subjects such as metallurgical castings.

In a scanning x-ray apparatus 12 of this general type the region of the subject 13 which is to be imaged is situated between at least one small radiation detector 14 and an x-ray source or tube 16 which produces a moving x-ray origin point 17. X-ray tube 16 may have a broad x-ray transmissive primary anode plate 18 spaced from an electron gun 19 which includes an electron emmissive cathode 21 heated by a filament 22, the region between the primary anode and cathode being within a vacuum envelope 25. To provide an electrical field for accelerating electrons from cathode 21 to primary anode 18, the cathode is connected to a negative terminal of a high voltage supply 23 through a variable resistor 24, the positive terminal of the high voltage supply and primary anode 18 being electrically grounded. Further elements of the electron gun 19 include a control grid 26 to which a variable voltage may be applied to control electron beam current, a first electron gun anode grid 27, and a focusing grid 28 situated between elements of a double gridded second electron gun anode or ultor 29, such elements being progressively more distant from the cathode 21 in order to accelerate and focus electrons into a narrow beam directed towards the primary anode plate 18. A high resolution electron gun, as employed in high resolution cathode ray tubes, may also be used. For this purpose high voltage supply 23 applies voltages to the first and second electron gun anode grids 27 and 29 which are progressively less negative, relative to ground, than the voltage applied to cathode 21 and further applies a voltage to focusing grid 28 which is more negative than that applied to the second anode grid 29. Control grid 26 receives a beam intensity control voltage through an optical coupler 31 as will hereinafter be described in more detail.

Figure 2:
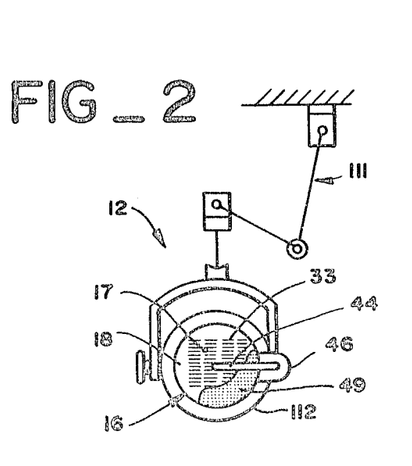
FIG. 2 is a diagrammatic view of suitable support and positioning structure for an x-ray source used in the system of FIG. 1.

The x-ray tube 16 is further provided with beam deflection means 32 for sweeping the electron beam through a raster pattern on primary anode 18 to generate the moving x-ray origin point 17. Referring to FIG. 2, the origin point 17 may typically be swept successively along a series of parallel scan lines 33 to define the raster pattern. For clarity of illustration, the number of scan lines 33 shown in FIG. 2 is much less than is usually the case and the spacing of the scan lines is exaggerated.

Referring again to FIG. 1, the beam deflection means 32 of this example is of the magnetic form having X and Y deflection coils, 34 and 36 respectively, for deflecting the electron beam in two orthogonal directions. As the deflection of an electron beam passing through the field of such deflection coils 34 and 36 is determined by the magnitude of current applied to the coil, the electron beam may be made to repetitively scan across primary anode plate 18 in the X axis direction by applying a repetitive ramp signal voltage to X deflection coil 34 and the successive scans in the X direction may be made to occur along a sequence of parallel scan lines by simultaneously applying a ramp signal voltage, which changes more slowly, to the Y deflection coil 36. For this purpose an X sweep frequency generator 37 is connected to one end of X deflection coil 34 through a variable resistor 38, the other end of the coil being connected to ground through another variable resistor 39. X sweep frequency generator 37 repetitively produces a ramp signal or voltage which rises at a selectable rate and then drops abruptly and in which the base level and amplitude of the rise may be selected in order to control the starting position and breadth of the scan in the X direction. Similarly a Y sweep frequency generator 41 is connected to one end of Y deflection coil 36 through an adjustable resistor 42, the other end of deflection coil 36 being grounded through an adjustable resistor 43. Y sweep frequency generator 41 produces a ramp signal which rises more gradually from a selectable base level to a selectable amplitude and then drops abruptly to the base level, so that the electron beam is shifted a relatively slight distance in the Y direction in the course of each scan in the X direction to thereby produce the desired raster pattern of a sequence of substantially parallel scan lines at primary anode 18. By adjusting the base level of the Y sweep frequency signals, the location of the initial scan line of the raster on anode plate 18 may be controlled and by adjusting the amplitude of the Y sweep ramp signal the height of the raster pattern in the Y direction may be controlled.

Radiation detector 14 generates detector signals in response to received X rays either on an individual pulse basis, where the intercepted radiation flux averages sufficiently low that individual X rays may be distinguished, or which produces a continuing signal of varying magnitude indicative of the level of intercepted radiation flux in instances where a number of X rays are usually being intercepted at any given time. While a variety of other radiation detectors may be adapted to this purpose, the detector 14 in this example is a very small scintillation crystal, such as a thallium doped sodium iodide crystal, of the type which produces scintillations of visible light in response to intercepted X rays. Such scintillations of light are transmitted by a light pipe 44 to a photomultiplier tube 46 which converts the light impulses into electrical detector signals. The detector signals may be discrete pulses under conditions where the x-ray flux intercepted by detector 14 has a low average value or may be a continuous electrical voltage the amplitude of which varies as a function of the number of X rays being intercepted by detector 14 at any given time. Photomultiplier 46 has an output terminal 47 connected to ground through a load resistor 48 across which the detector signals are developed. Where the scanning x-ray apparatus 12 is designed for dental usage as in this example, it is advantageous if the light pipe 44 which transmits light impulses from detector 14 to photomultiplier 46 has a curved configuration to form a probe which may be inserted into the mouth of the dental patient.

Although not strictly essential in order to produce image data, a focussing collimator 49 may be situated between the x-ray tube 16 and the subject 13 to reduce radiation dosage and to enhance image clarity. Collimator 49 may be one or more plates or laminations of radiation absorbent material transpierced by a large number of minute radiation transmissive passages 51 each directed towards the detector 14. For clarity of illustration, the collimator 49 is depicted in FIG. 1 with a much smaller number of passages 51 than are typically present, passage diameters and spacings of the order of microns being most preferrable. The collimator 49 reduces radiation dosage by suppressing X rays which are not traveling towards the detector 14 and therefore could not contribute image data. The collimator 49 enhances image clarity by suppressing secondary X rays which do not originte at the moving origin point 17 and which could introduce spurious data into the image.

As the x-ray origin point 17 sweeps along successive scan lines of the raster pattern, the electrical pulse rate or voltage at detector output terminal 47 varies in accordance with changes of x-ray transmissivity at successive regions of the subject 13. Thus the detector signals at terminal 47 in conjunction with the X and Y positional signals, appearing across resistors 39 and 43 respectively, contain the data needed for generation of one or more radiographic images of the scanned region of the subject 13. The signal processing system 11 enables simultaneous presentation of a plurality of radiographic images from a given exposure of the subject 13, each of which may emphasize a different aspect of the scanned region of the subject and some of which may contain data which was suppressed from the detector signals in producing others of the images.

The images may be displayed at a plurality of X-Y display means of which a first, second, third and fourth display means, 52, 53, 54 and 55 respectively, are provided in this example although additional display means for simultaneously imaging still other aspects of the subject may also be provided. The X-Y display means 52 to 55 of this example are cathode ray tube oscilloscopes of the known type which have X and Y sweep frequency terminals 56 and 57 respectively for controlling an electron beam sweep raster pattern at a screen 58 and having a Z or beam intensity terminal 59 to which a variable voltage may be applied to vary electron beam intensity at the screen in the course of the raster scanning in order to produce a visible image at the screen. Television receiver sets equipped with scan converters or other X-Y display devices of known forms may also be used in place of the oscilloscopes 52 to 55.

To provide identical X and Y sweep frequency signals to each of the oscilloscopes 52 to 55, corresponding to the movement of the x-ray origin point 17 at x-ray tube 16, the X sweep frequency terminal of each oscilloscope is connected to an X sweep frequency conductor 61 while the Y sweep frequency terminal 57 of each oscilloscope is connected to a Y sweep frequency conductor 62. The X sweep frequency signals, taken from the circuit junction between X deflection coil 34 and resistor 39 may be applied to conductor 56 through an amplifier 63 by closing a switch 64. Similarly, the Y sweep frequency signals taken from the junction between Y deflection coil 36 and resistor 43 may be applied to conductor 62 through an amplifier 66 by closing a switch 67.

The signal processing system 11 enables presentation at the screen 58 of first display means 52 of a radiographic image emphasizing changes of x-ray transmissivity in the subject which have a predetermined selected spatial frequency. The term spatial frequency refers to the degree of abruptness and persistence of an x-ray transmissivity change in the subject along the direction of the scan. A change of x-ray transmissiveness between adjoining regions of the subject which occurs relatively gradually or which persists for a sizable distance may be said to have a low spatial frequency. A relatively abrupt or brief change of x-ray transmissivity along the direction of the scan has a high spatial frequency. Spatial frequency differs from contrast which is a measure of the magnitude of the change of x-ray transmissivity between two regions of the subject. Thus in the examination of a medical patient for example, the difference in x-ray transmissivity or contrast between a region of tumorous tissue and adjoining healthy tissue may be very small but if the boundary is abrupt the transition has a high spatial frequency. On the other hand the differences of x-ray transmissivity or contrast of adjoining regions of bone structures within the medical patient may be very sizable but the change may not be abrupt and thus may have a low spatial frequency. If the x-ray origin point 17 moves at a uniform rate, then a high spatial frequency change in the subject 13 is one which causes the detector 14 signal to change in a brief time period while a low spatial frequency change produces a relatively slow change and/or a sustained change of the detector signal.

By adjusting the signal processing system 11 to suppress low spatial frequencies an image may be obtained at the first display means 52 which exhibits an edge enhancement effect emphasizing boundaries between adjoining regions of the subject which may in some cases differ only slightly in radiopacity or x-ray transmissiveness. Conversely, by suppressing high spatial frequencies, the image may be caused to display only sustained transmissivity differences that extend over a broad region of the subject.

Considering now suitable circuits for processing the detector signals to provide spatial frequency filtering, feedback circuit means defined by a feedback circuit 68 is coupled between the detector signal terminal 47 and the control grid 26 of the x-ray tube 16 for producing a feedback signal which regulates the x-ray tube to maintain the average value of the detector signals substantially constant while enabling brief variations of the detector signal in response to scanning across abrupt, high spatial frequency boundaries between regions of the subject. Variations of the x-ray detector signal which would otherwise result from scanning across more gradual, low spatial frequency boundaries and sustained variations which may follow an abrupt boundary are thereby suppressed from the x-ray detector signal.

The feedback circuit 68 in this example has a differential amplifier 69 to which the detector signals from terminal 47 are applied through a preamplifier 70. The reference input of differential amplifier 69 receives a selectable DC voltage from a potentiometer 72. Potentiometer 72 is coupled to a regulated bipolar direct current power supply 73 which also supplies stabilized positive and negative voltages to the several other potentiometers of the system to be hereinafter described. For clarity of illustration, the connections between DC power supply 73 and potentiometer 72 and the other potentiometers to be hereinafter described are not shown in FIG. 1 and it should be understood that a plus sign (+) denotes a connection to the positive terminal of DC power supply 73 while a minus sign (−) indicates a connection to the negative terminal of the power supply.

As the fixed selected voltage applied to the reference input of differential amplifier 69 is subtracted from the voltage applied to the other input of the amplifier, amplifier 69 serves to eliminate voltage fluctuations of less than a predetermined selectable magnitude which typically arise from extraneous causes and are not indicative of meaningful image information. In addition to suppressing circuit noise, amplifier 69 amplifies and shapes the detector signals for transmission to a first signal integrating means 71 having a variable, selectable time constant. First signal integrating means 71 has a variable resistor 74 and a variable capacitor 75 connected in series between amplifier 69 and ground. The output impedance of amplifier 69 has a low DC value in comparison with the maximum resistance of variable resistor 74 and thus the time constant of integration may be selected by adjustment of resistor 74 and capacitor 75. Owing to the integrating effect of the R-C network defined by the resistor 74 and capacitor 75, the voltage on the capacitor does not change significantly in response to individual pulses or abrupt voltage variations but does rise or fall in response to sustained increases or decreases in the average magnitude of the detector signals from terminal 47. This voltage on capacitor 75 is applied to another differential amplifier 76 which has a reference input receiving a selectable DC voltage from another potentiometer 77. The output of amplifier 76, at a terminal 99, is a feedback signal voltage having an average level or base line which may be selected by adjustment of potentiometer 77 and which varies in proportion to the average value of the detector signals from terminal 47 but which does not vary significantly in response to brief fluctuations of the detector signals.

The output voltage from amplifier 76 is superimposed upon the cathode voltage from high voltage supply 23 and applied to the control grid 26 of x-ray tube 16 through optical coupler 31 and an inverting amplifier 80. As the control grid 26 voltage determines electron beam current within the x-ray tube 16, the effect of the feedback signal is to maintain the average level of x-ray flux received by detector 14 at a substantially constant value irrespective of changes of x-ray transmissiveness at different regions of the subject 13. If the x-ray flux being received by detector 14 undergoes an increase which is sustained for a period of time determined by the setting of resistor 74, then the voltage at control grid 26 becomes more negative to decrease electron beam current within the x-ray tube 16 thereby restoring the average value of the detector signal at terminal 47 to the value which was selected by adjustment of resistor 74. If the level of x-ray flux being received at detector 14 decreases in a similarly sustained manner, then the voltage at control grid 26 changes in the positive direction to increase electron beam intensity and thereby maintain the radiation flux at detector 14 at the selected average value. Thus the effect of the feedback circuit 68 is to suppress, from the detector signal at terminal 47, voltage fluctuations indicative of low spatial frequency changes between adjoining regions of the subject 13. Only high spatial frequency changes in the subject 13, indicative of relatively abrupt boundaries between adjoining areas of different x-ray transmissivity, are able to cause a fluctuation of the detector signal voltage at terminal 47.

While regulation of x-ray output in this example of the invention is accomplished by using the feedback signal to vary the voltage at control grid 26, it is also possible to accomplish a similar result by varying the cathode 21 voltage in accordance with the feedback signal by utilizing a programmable high voltage supply. Variation of the cathode 21 voltage regulates electron beam energy rather than intensity or current but either form of variation of the electron beam causes a change of x-ray production at origin point 17. X-ray production may also be varied in response to the feedback signals by a combination of beam intensity and beam energy control.

The detector signals from terminal 47 are processed and transmitted to the first display means 52 through a first image signal circuit 78.

First image signal circuit 78 has two alternate modes of operation as determined by the setting of mode control switch 79. Under the first or nonintegrating mode of operation the circuit 78 serves to establish a selectable base level and maximum amplitude for the detector signals from detector output terminal 47 and to provide an adjustable degree of amplification after which the shaped and amplified signals are transmitted to the Z or intensity signal terminal 59 of the first display means 52. Provided that switches 64 and 67 are closed to transmit the X and Y sweep frequency signals to display means 52, a radiographic image is then generated on the screen 58 of display means 52 which is indicative of abrupt variations of x-ray transmissiveness in different portions of the scanned region of the subject 13 except that low spatial frequency variations which occur relatively gradually in space and variations which persist for a sizable distance in the direction of the scan following an abrupt change may be suppressed by the action of the feedback circuit 68. Thus the image at display means 52 exhibits edge enhancement of the boundaries between regions of the subject of different radiopacity.

In the alternate or integrating mode of operation, the first image signal circuit 78 performs the functions identified above but also integrates or averages the detector signal fluctuations from output terminal 47 over a selectable time period. This integrating mode of operation may be used under either or both of two different circumstances. First, the integrating mode may be used where the rate of interception of individual X rays at detector 14 is sufficiently high that individual counts cannot be distinguished and processed on a pulse basis. Where such pulse pile up occurs, the integrating function results in a continuous output voltage which varies in amplitude according to the average rate of receipt of X rays at detector 14 during the preceding brief time interval. The first image signal circuit 78 is also operated in the integrating mode where it is desired to suppress data indicative of abrupt or high spatial frequency changes of X-ray transmissivity in the subject 13 in order to emphasize the more gradual changes and sustained changes which may occur between adjoining regions of subject 13. If variable resistor 74 and variable capacitor 75 of feedback circuit 68 are adjusted to substantially eliminate the integrating function in the feedback circuit while the first image circuit 78 is adjusted to provide a selectable degree of signal integration, than the two circuits in conjunction function as a high spatial frequency blocking filter and the only data appearing at the screen of display means 52 is data indicative of gradual or sustained transitions in the subject 13. If feedback circuit 68 is adjusted to suppress data indicative of spatial frequency changes of less than a predetermined extent while first image circuit 78 is adjusted to suppress data indicative of a selected range of relatively high spatial frequencies, then the two circuits in conjunction function essentially as a spatial frequency band pass filter.

In order to perform the above described functions, the first image signal circuit 78 may have an adjustable gain preamplifier 81 receiving detector signals from terminal 47 to shape the detector signals and to provide a selectable degree of amplification. The output of preamplifier 81 is coupled to one input of a differential amplifier 82 which has a second input receiving a selectable DC reference voltage from a potentiometer 83. Differential amplifier 82 eliminates signal fluctuations of less than a predetermined amplitude, selected by adjustment of potentiometer 83 and thus enables the suppression of circuit noise or minor voltage fluctuations which are not indicative of the desired image data. At a first setting of control switch 79 to establish the first or nonintegrating mode of operation, the output signals of amplifier 82 are transmitted directly to an adjustable signal amplitude limiter 84 which is an amplifier in this example although other components such as a monostable gating device may be used in some instances. At the alternate setting of control switch 79, a second adjustable time constant integrating means 86 is present in the signal path from amplifier 82 to switch 79. More specifically, a variable resistor 87 and a variable capacitor 88 are connected in series between the output of amplifier 82 and ground, the junction between resistor 87 and capacitor 88 being connectable to amplitude limiting amplifier 84 through the control switch 79 when the control switch is at the alternate setting. Thus resistor 87 in conjunction with capacitor 88 forms a signal integrating or averaging R-C network, the time constant of which may be selected by changing the resistance of the variable resistor 87 or the capacitance of capacitor 88 or both. The effect of the second integrating means 86 is to block relatively abrupt or brief signal voltage fluctuations from amplifier 84 while enabling more gradual or sustained changes of signal amplitude to be transmitted on through amplifier 84.

A resistor 89 is connected between the output of amplifier 84 and ground and has an adjustable voltage tap 91 connected to a first image signal terminal 92 which is connected to intensity signal terminal 59 of first display means 52 and also to other components of the signal processing system 11 to be hereinafter described. By movement of voltage tap 91 along resistor 89, the gain of the first signal circuit 78 may be adjusted in order to match output voltage ranges with the required Z or intensity signal ranges of the display means 52.

As described above, the feedback circuit 68 and/or the first image signal circuit 78 may be used to suppress certain data about the scanned region of the subject 13 from the first image signals supplied to first display means 52. This can be highly advantageous as the suppressed data might otherwise obscure other aspects of the subject which are to be emphasized in the image at the first display means 52. At the same time, it may also be desirable to produce radiographic images, from the same scanning of the subject 13, that include some or all of the data which was suppressed from the first image signal. While that portion of the data which is suppressed by the first image signal circuit 78, when it is operated in the integrating mode, remains present in the detector signals at output terminal 47, this is not true of that portion of the data which may be suppressed by the feedback circuit 68. The low spatial frequency information which is suppressed by the feedback circuit 68 is absent from the detector signals at terminal 47 as it has been eliminated by controlling the x-ray tube 16 itself to prevent such information from registering at the detector 14. Some or all of this eliminated data may be needed to enable presentation, at the additional display means 53, 54, 55, of additional images of different selected contrast ranges in order to emphasize changes of x-ray transmissivity in the subject of different relative magnitudes.

Accordingly second image signal circuit 93 is provided to generate a second image signal at an output terminal 94 which contains contrast data about the scanned region of the subject 13 which may have been suppressed from the detector signal at terminal 47 by the feedback circuit 68 and which may contain the total range of contrast information available from the scanning of the subject 13 provided that the first image signal circuit is operating in the nonintegrating mode.

The second image signal is generated by a second image signal circuit 93 including signal combining means for combining the feedback signal from feedback circuit 68 with the first image signal from circuit 78. Second image signal circuit 93 has a differential amplifier 97 for algebraically summing the two signals, one input of the summing amplifier 97 being connectable with first image signal terminal 92 by closing a switch 98. The other input of summing amplifier 97 is connectable to output terminal 99 of the feedback circuit 68 through an inverting amplifier 101 by closing an additional switch 99.

The output voltage of summing amplifier 97 at an output terminal 94 is a second image signal containing the contrast data which was suppressed from the first image signal by the action of feedback circuit 68. Provided that the first image signal circuit 78 is being operated in the nonintegrating mode, with switch 79 positioned to communicate amplifier 82 directly with amplifier 84, this second image signal contains the full range of contrast information realizable from the given scanning of the subject 13. This full range signal is transmitted to the Z or intensity signal terminal 59 of second display means 53 causing that display means to generate a standard radiographic image containing the full range of contrasts and spatial frequencies.

Second display means 53 does not visibly display the total information about the subject 13 obtained from the x-ray scanning. The gray scale or contrast latitude range of display devices such as the oscilloscope 53 is much more limited than the range of contrast variations developed by scanning many subjects 13. The screen 58 of a typical cathode ray tube cannot accommodate to and display variations in brightness or gray scale level of more than a factor of about one hundred. This relatively limited dynamic range is also characteristic of other image presentation means and also of the photographic film which may be used to record the displays at the screens 58. Accordingly, the signal processing system 11 further provides for simultaneous generation of additional radiographic images displaying transmissivity changes in the subject that may not be visible in the full contrast range image at second display means 53. The additional images may collectively exhibit a contrast range greater than can be made visible at any single display means. In particular, third image circuits 102a and 102b provide for selecting and transmitting to separate additional display means such as third display means 54 and fourth display means 55, different selectable portions of the total range of contrast data contained in the second image signal at terminal 94. Thus information contained in the second image signal which cannot be effectively presented on any one display means due to contrast range limitations, may be distributed over a plurality of display means.

Third image signal circuit 102a of this example includes a first differential amplifier 103a having one input coupled to second image signal terminal 94 and having the other input coupled to a potentiometer 104a. Amplifier 103a transmits, to one input of an output differential amplifier 106a, only the portion of the second image signals which exceed a lower voltage limit that is selectable by adjustment of potentiometer 104a. A second differential amplifier 107a has one input coupled to second image signal terminal 94 and the other input coupled to another potentiometer 108a providing a selectable reference voltage. Amplifier 107a transmits, to the other input of output amplifier 106a, only the portion of the second image signals which exceed an upper voltage limit selected by adjustment of potentiometer 108a. The output amplifier 106a subtracts the voltage range transmitted by amplifier 107a from that transmitted by amplifier 103a and the output is transmitted to the Z or intensity signal 59 of third display means 54. Thus, by adjustment of potentiometers 104a and 108a, window or range of signal amplitudes may be selected out of the total range of signal amplitudes available at terminal 94. The selected range of signal amplitude variations is amplified at amplifier 106a and applied to the Z terminal of third display means 54 to produce a third radiographic image having selected contrast characteristics differing from those of the images being displayed by the first and second display means 52 and 53.

The additional third image circuit 102b enables simultaneous presentation at the fourth display means 55 of still another radiographic image exhibiting different selected contrast characteristics and may be similar to the first third image circuit 102a described above. Thus, the third image signal circuit 102b has a first differential amplifier 103b with one input coupled to terminal 94 and the other input coupled to a lower signal amplitude limit selector potentiometer 104b. A second differential amplifier 107b has one input coupled to terminal 94 and the other input coupled to an upper signal amplitude selector potentiometer 108b. An output differential amplifier 106b receives the output voltages from both amplifiers 103b and 107b and provides the Z or intensity signal to terminal 59 of the fourth display means 55.

As will be apparent, still additional ones of the third image signal circuits, such as circuits 102a and 102b, may be provided to present additional images on additional display means that make visible still other selected portions of the total contrast information contained in the second image signals.

To minimize radiation dosage of the subject of enabling shutting down of the x-ray tube 16 after a single scanning raster or limited number of scanning rasters have been completed, without thereby ending the presentation of the images at the display means 52 to 55, the display means are preferrably of the form having persistence controls for causing images to continue to be presented at the screens 58 after the images have been initially generated. Thus the scanning of the subject 13 need not be continued, after the desired information has been initially generated, while the images are being studied. Where a more permanent record of one or more of the images is desired the presentations at the screens 58 may be photographed.

While the several display means 52 to 55 have been herein described as being separate oscilloscopes, usage may also be made of cathode ray tube display devices of the type having plural screens for displaying different images or having the capability of displaying different plural images on a single screen.

The additional display means 109a and 109b, which may also be cathode ray tube oscilloscopes or a single dual image oscilloscope, enable use of the first image signals from terminal 92 to facilitate the positioning of the x-ray tube 16 and detector 14 relative to the subject 13 in preparation for an exposure. The additional display means 109a and 109b also facilitate a later duplicating of the same positioning of the x-ray tube 16, detector 14, and subject 13 if it is desired to compare images made at a first time with subsequent images taken at a later date. Referring again to FIG. 2, the x-ray tube 16 together with collimator 49, photomultiplier 46 and detector probe 44 may be mounted in a support linkage 111 of the known form, commonly used to support older forms of dental or medical x-ray tube, which has a plurality of lockable pivot and swivel joints that enable the x-ray tube to be maneuvered into a desired angular orientation relative to the subject in both horizontal and vertical directions and which enable raising, lowering and advancement or retraction of the x-ray tube relative to the subject. The support means 111 preferably further includes means such as a bearing ring 112 enabling the x-ray tube 16 to be turned angularly about the central longitudinal axis of the x-ray tube.

Referring now to FIGS. 1 and 2 in conjunction, the additional display means 109a and 109b enable the operator to maneuver the x-ray tube 16 so that a desired selected portion of the dentition of the subject 13 will be depicted in the images in a desired orientation on the screens of the display devices. For this purpose the Z or intensity signal terminals of both display means 109a and 109b are coupled to separate potentiometers 113a and 113b respectively which may be adjusted to control the brightness of the images to be presented on the screens 114a and 114b respectively of the two display screens. The Y sweep frequency terminal 116a of display means 109a is coupled to Y sweep frequency conductor 62 and the X sweep frequency terminal 117b of display means 109b is coupled to the X sweep frequency conductor 61. The X sweep frequency terminal 117a of display means 109a and the Y sweep frequency terminal 116b of display means 109b are both coupled to the first image signal terminal 92.

Figure 3A:
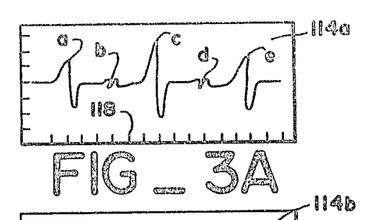
FIGS. 3A and 3B are depictions of graphical wave forms which may be generated by the system of FIG. 1 for facilitating positioning of the x-ray source in relation to a subject to be examined.
Figure 3B:
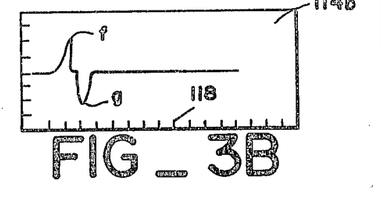

The dental technician or other operator actuates the scanning x-ray tube 16, preferably at a low level of x-ray output, and views the screens 114a and 114b in order to check the position of the x-ray tube 16 and detector 14 relative to the subject 13. For purposes of example FIGS. 3A and 3B depict the wave forms visible on the screens of display means 109a and 109b respectively when the x-ray tube 16 and detector 14 are correctly positioned to image the two lower incisor or front teeth of a dental patient subject 13. In FIG. 3A, which depicts the screen 114a of display means 109a, the three major peaks a, c and e of the displayed waveform correspond to passage of the scan across the gaps or boundaries between the incisor teeth and adjacent teeth, the central peak c being indicative of the passage of the scan across the boundary between the two front incisor teeth themselves. The lesser peaks d and b visible in the waveform correspond to passage of the scan across the nerve canals within the two teeth. By shifting the x-ray tube 16 including detector 14 to locate a peak c midway between the sides of screen 114a, the operator assures that the preferred positioning of the apparatus relative to the subject 13 has been arrived at. Referring now to FIG. 3B, the waveform having peaks f and g visible on the screen 113b of the other additional display means 109b facilitates positioning of the x-ray tube 16 and detector 14 in the vertical direction relative to the subject. The signal amplitude peaks f and g occur as the Y or vertical scan passes between the lower and upper teeth of the subject, the small displacement between the two peaks f and g in this example being caused by the jaws being slightly open to receive the detector probe. By shifting the apparatus to cause the peaks f and g to be near the start of the waveform at one side of the screen 114b, the operator is assured that the two lower front incisor teeth will be fully imaged. The presentations on the screens 114a and 114b also facilitate angulation of the x-ray tube relative to the subject to assure that the plane of the scanning raster is parallel to the desired image plane. The peaks a to e on screen 114a of FIG. 3A and peaks f and g of FIG. 3B become of maximum amplitude when the raster pattern area or anode plate 18 of the x-ray tube 16 of FIG. 1 is parallel to the image plane through the two front incisor teeth.

Provided that the screens 114a and 114b depicted in FIGS. 3A and 3B respectively are of the form having horizontal and vertical calibration markings 118, the positions of the peaks a to g may be recorded so that the exposure geometry may be reconstructed at a later date to obtain later images which may be precisely compared with those produced at an earlier time.

Referring again to FIG. 1 in particular, use of the additional display means 109a and 109b for facilitating positioning and repositioning of the x-ray tube 16 and detector 14 relative to the subject 13 has been described with particular reference to dental x-ray apparatus, for purposes of example only. The additional display means 109a and 109b may be used in an essentially similar manner to facilitate positioning and repositioning relative to other subjects to be imaged, such as portions of the anatomy of medical patients or inanimate subjects such as metallurgical castings. Most such subjects have configurations which cause characteristic locational peaks to be produced on the screens of the additional display means 109a and 109b.

It has been pointed out that the data displayed on any or all of the several display means 52 to 55 may be recorded, for layer study, by photographing the screens 58. Alternately or supplementally, it may be desirable to store the processed signals for later playback and display at the display means 52 to 55. For this purpose, signal data storage means 121 provides for selectively storing the first image signals from first image signal circuit 78, the feedback signal from circuit 68 and the X and Y sweep frequency signals. The data storage means 121 may subsequently return some or a selected portion of the stored signals to appropriate points in the signal processing system 11 for later presentation of any or all of the several types of radiographic image described above.

Data storage 121 may have a first image signal input 122 connectable to first image signal terminal 92 by closure of a switch 123 and may have a feedback signal input 124 connectable to feedback signal terminal 99 by closure of another switch 126. An X sweep frequency signal input 127 is connectable to X sweep frequency conductor 61 by closure of a switch 128 and a Y sweep frequency signal input 129 is connectable to Y sweep frequency conductor 62 by closure of a switch 131. The several switches 122, 126, 128 and 131 may be closed simultaneously at the start of a scanning of the subject 13 to store the information needed for later playback and display of any or all of the several types of radiographic images. If it is not desired to produce instantaneous images at the several display means 52 to 55 while signal information is being stored, switches 98 and 99 may be opened during the scanning of the subject 13.

Figure 4:
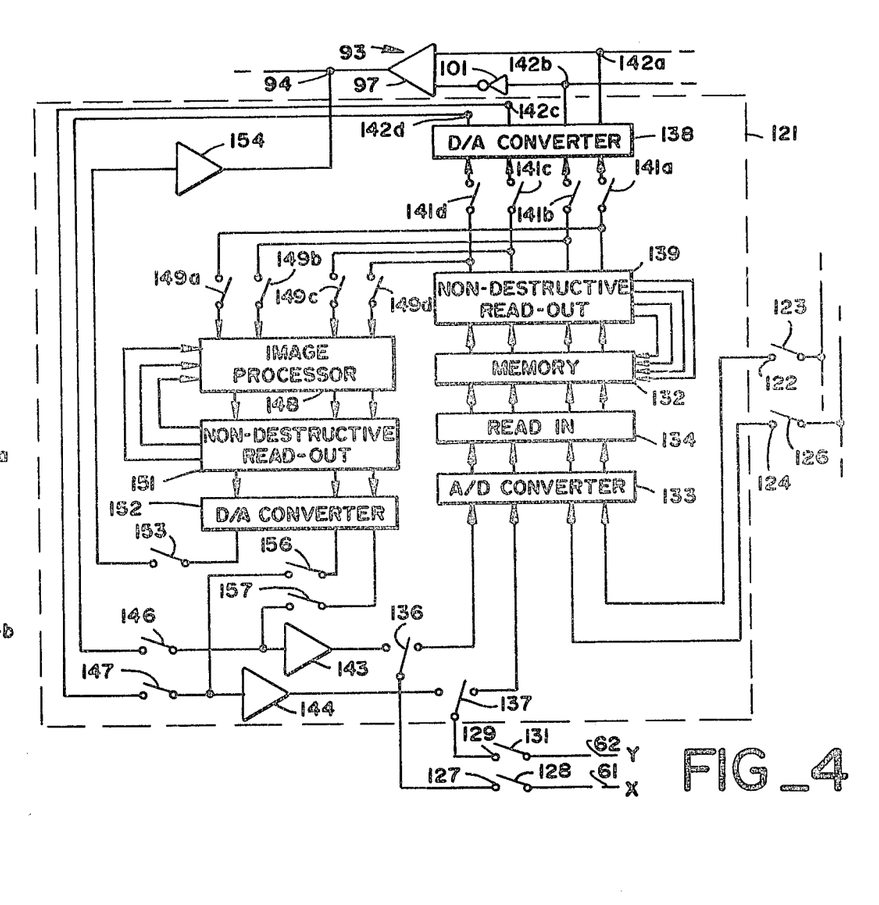
FIG. 4 is a schematic circuit diagram depicting a data storage and readout which may be used in conjunction with the apparatus of the preceding figures.

While the data storage 121 may employ analog signal storage and playback techniques, such as magnetic tape, a digital system as depicted in FIG. 4 is advantageous. First image signal input 122, feedback signal input 124, Y sweep frequency signal input 129 and X sweep frequency input 127 may each be coupled to a digital storage unit or memory 132 through the first to fourth channels respectively of a four channel analog to digital signal converter 133 and a four channel read-in circuit 134. X and Y sweep frequency signal inputs 127 and 129 respectively are connected to the analog to digital converter 133 through additional two position switches 136 and 137 respectively. Switches 136 and 137 have alternate positions for feeding back the stored X and Y sweep frequency signals to X and Y sweep frequency conductors 61 and 62 respectively as will hereinafter be discussed in more detail.

Memory 132 is coupled to a four channel digital to analog signal converter 138 through a four channel readout circuit 139 which is preferably of the nondestructive form that restores data in memory 132 as it is extracted and delivered to convertor 138. The four information channels between readout circuit 139 and digital to analog converter 138 include switches 141a, 141b, 141c and 141d which may be opened under certain modes of operation to be hereinafter described.

The first channel output terminal 142a of converter 138 is connected to the first image signal input of amplifier 97 of the second image signal circuit 93. The second output terminal 142b of converter 138, delivering the reconstructed feedback signal, is connected to the input of inverter amplifier 101 of the second image signal circuit 93. The third and fourth outputs 142c and 142b respectively from converter 138, which transmit the reconstructed analog Y sweep frequency signal and X sweep frequency signal respectively, are connectable to the inputs of amplifiers 143 and 144 respectively through switches 146 and 147 respectively. The outputs of amplifiers 143 and 144 return the reconstructed sweep frequency signals to Y sweep frequency conductor 62 and X sweep frequency conductor 61 respectively when switches 136 and 137 are set at the alternate switch positions.

Referring to FIG. 1 in conjunction with FIG. 4, the components of the data storage 121 which have been described up to this point enable the storing, in digitized form, of the first image signal from circuit 78 and the feedback signal from feedback circuit 68 together with the associated scan position information defined by the X and Y sweep frequency signals. When the stored data is to be recovered and displayed at a later time, switches 141a to 141d and switches 146 and 147 are closed and switches 136 and 137 are shifted to the alternate positions to connect the outputs of amplifiers 143 and 144 respectively with X and Y sweep frequency conductors 61 and 62 respectively through closed swiches 128 and 131. The data storage 121 is thereby conditioned to reconvert the stored signals to analog or voltage form for delivery to the second image signal circuit 93 and X and Y sweep frequency conductors 61 and 62. Radiographic images emphasizing different aspects of the scanned subjects are then produced on the second, third and fourth display means 53, 54 and 55 respectively in the manner previously described. Further, since the stored data may be repetitively redelivered by the data storage 121, the contrast range selection potentiometers 104a, 108a, 104b and 108b may be readjusted between successive playbacks of the stored data in order to generate additional images of different selected contrast range that could not be produced simultaneously during the original scanning of the subject 13 because of the limited number of display means available.

If it is desired to generate radiographic images containing only the high spatial frequency portion of the image data, switch 141a of the data storage 121 may be left open while the associated switches 141b, 141c and 141d are closed to return the stored data to the signal processing system 11. Similarly, if it is desired to generate images containing only the low spatial frequency data, switch 141*b* may be left open while switches 141*a*, 141*c* and 141*d* are closed.

In the portion of the data storage 121 described above, the image signals which are initially in analog form are converted to digital form signals for storage. The digitized data is later reconverted back to analog or voltage signals for delivery to the inputs of the second image signal circuit 93 which then recombines the high and low spatial frequency analog signals to produce full contrast range signals. Alternately this recombination of the high and low spatial frequency data may be effected digitally within the data storage 121 itself and the data may be modified for special purposes such as by selecting and enlarging a specific portion of the total scanned area for example. The digitally reconstructed full contrast range signal may then be converted to analog form and be delivered directly to output terminal 94 rather than using the second image signal circuit 93 to perform the recombination of the high and low frequency portions of the data. For this purpose an image processor computer 148 of known construction and operation may have four data input channels each connected to a separate one of the output channels of readout 139 through a separate switch 149*a*, 149*b*, 149*c* and 149*d*. Upon closing of the switches 149*a* to 149*d*, with switches 141*a* to 141*d* open, readout 139 may be caused to transmit the image signal data including the associated X and Y positional data which is stored in memory 132 to the image processor 148. Processor 148 sums and stores the digital data received through the first and second channels defined by switches 149*a* and 149*b* and thus may store a reconstructed full contrast range signal in digital form. As the high and low spatial frequency image data is combined in processor 148, the processor requires only three output channels which are coupled to an additional nondestructive readout 151. A three channel digital to analog signal converter 152 converts the data extracted from processor 148 by readout 151 to analog or voltage form and by, closing a swich 153, the analog full contrast range signal is transmitted to terminal 94 through an adjustable gain amplifier 154. Simultaneously, by closing additional switches 156 and 157, the reconstructed stored X and Y sweep frequency signals are delivered to the inputs of amplifiers 144 and 143 respectively for return to the X and Y sweep frequency conductors 61 and 62 through switches 136 and 137 and 128 and 131. Referring again to FIG. 1, radiographic images making visible different contrast information from the scanned region of the subject are then generated on the second, third and fourth display means 53, 54 and 55 in the manner previously described for the other modes of operation of the signal processing system 11.

Operation

Referring to FIGS. 1 and 2 in conjunction, production of plural radiographic images of a subject 13 from a single radiation exposure is initiated by positioning the x-ray tube 16 including collimator 49 and the detector 14 to locate the region of the subject which is to be imaged between the collimator and detector. Probe 44 maintains the detector 14 at the point of convergence or focal point of the x-ray passages 51 of the collimator. The jointed lockable support linkage 111 depicted in FIG. 2 may be utilized to hold the x-ray tube 16 including the collimator 49 and detector 14 in the selected relationship to the subject 13. Correct positioning of the apparatus relative to subject 13 may be facilitated and the positioning may be recorded for later duplication by making use of the positioning display means 109*a*, 109*b* and the waveforms generated on such display means as depicted in FIGS. 3A and 3B in the manner which has been previously described.

Referring again to FIG. 1, the scanning x-ray tube 16 is then operated to sweep the x-ray origin point 17 at least once through the scanning raster pattern. X rays are emitted in all directions from the origin point 17 but collimator 49 absorbs and suppresses X rays traveling in the general direction of the subject 13 other than X rays which are directed towards the small detector 14 and which can therefore contribute useful image data. At any given instant during the scanning operation, the signal produced by detector 14 is indicative of the x-ray transmissivity of the subject 13 along a line extending from the detector 14 to the position of x-ray origin point 17 at that instant. Thus the amplitude of the detector signal varies in accordance with variations of x-ray transmissivity between adjacent portions of the scanned region of the subject 13. Photomultiplier tube 46 converts such signals into electrical pulses or into a continuous electrical voltage of variable magnitude depending on the rate of x-ray reception at the detector 14. The electrical detector signals from photomultiplier 46 are impressed across load resistor 48 and are therefore available to the signal processing system 11 at detector signal terminal 47. Concurrently, electrical voltage signals having a varying amplitude indicative of the position of the x-ray origin point 17 at any instant are available to the signal processing system 11 from amplifiers 63 and 66 provided that switches 64 and 67 are closed.

If resistor 74 and capacitor 75 of the feedback circuit 68 are adjusted to establish a very long time constant for the first signal integrating means 71, then the integrating or signal averaging function within the feedback circuit 68 is increased to the point that the circuit output or feedback signal is essentially constant. Under that condition, the detector signals available at terminal 47 are indicative of the full range of contrasts or transmissivity variations developed by the scanning of the subject 13 without regard to whether or not such variations occur abruptly and briefly or occur gradually or are sustained. If, under that condition, the first image signal circuit 78 is set to the nonintegrating or averaging mode by setting switch 79 to connect amplifier 82 directly with amplifier 84, then the detector signals are shaped and amplified and transmitted to the Z or intensity signal terminal 59 of first display means 52. A lower portion of the signal amplitude variations, selectable by setting of potentiometer 83, is eliminated by amplifier 82 to remove minor circuit noise fluctuations which are not indicative of meaningful data. The amplification of the detector signal in circuit 78 is selectable by adjustment of the gain of amplifier 81 and an upper limit for signal amplitudes is determined by adjustment of the gain of amplifier 84. Adjustment of resistor tap 91 enables matching of the range of signal voltage variations to the range of voltages which can be accommodated by the image intensity circuit of display means 52.

Under the above described operating conditions, a visible radiographic image of the scanned region of the subject 13 is produced at screen 58 of display means 52 as the scanning raster of the display means is synchronized with that of the x-ray tube 16 while the image intensity at any given point on screen 58 is determined by the x-ray transmissivity of the corresponding portion of the scanned region of the subject. The image at display means 52 under the above described operating conditions includes the full detectable range of spatial frequency variations of x-ray transmissivity between different regions of the subject 13 but does not make visible all of the information about the subject which may be desired and which is potentially available from the scanning of the subject. The range of x-ray transmissivity variations or contrast in many subjects 13 is more extensive than the range of image contrast available at the screen 58 of a display means 52. Depending on the adjustment of the contrast controls of the display means 52, either small changes of transmissivity in the subject may be obscured by an adjustment which makes large changes visible or the large changes may appear as seemingly small transmissivity changes.

Under the above described operating conditions, the second image signal circuit 93 and second display means 53 may be used to simultaneously generate a second radiographic image in which a different range of transmissivity changes within the subject is made apparent from the same scanning. Although under the operating conditions described above the second image signal at terminal 94 does not differ significantly in information content from the first image signal at terminal 92, the contrast controls of the second display means 53 may be adjusted to emphasize a different selected range of subject transmissivity variations. Additional simultaneous radiographic images from the same scanning of the subject, each emphasizing a different range of transmissivity or control variations may be displayed at the third and fourth display means 54 and 55. Potentiometers 104a and 108a may be adjusted to cause third display means 54 to present an image in which transmissivity changes in the subject within a first selected limited range are visible while potentiometers 104b and 108b may be adjusted to cause the fourth display means 55 to present an image making visible a still different limited range of transmissivity variations in the subject. By adjustment of the potentiometers 104a, 108a, 104b and 106b, these limited ranges of transmissivity variation or contrast may be selected to be narrow or broad and may be separated bands of the full range of detected transmissivity variations or may be overlapping ranges. Also, one range displayed at display means 54 for example, may be a very narrow one contained within a broader range displayed at display means 55.

If desired, swiches 123, 126, 128 and 131 may be closed at the commencement of the scanning operation to store the processed detector signals from terminal 92, the feedback signal, if any, from circuit 68 together with the X and Y sweep frequency signals from conductors 61 and 62. The stored signals may later be returned to the signal processing system 11 for subsequent image production in the manner which has previously been described.

Considering now the operation of the system 11 in the spatial frequency selection mode, voltage changes at detector signal terminal 47 which would otherwise result from subject transmissivity variations which occur gradually in space or which are sustained in time may be suppressed by adjusting resistor 74 of feedback circuit 68 to decrease the time constant of the first integrating means 71. The feedback circuit 68 then integrates or averages incoming detector signals to produce an output voltage or feedback signal at terminal 99 which varies in accordance with changes in the average amplitudes of the incoming detector signals but which does not vary significantly in response to relatively abrupt or brief changes of detector signal amplitude. Within optical coupler 31, the feedback signal voltage from circuit 68 is added to the cathode voltage from high voltage supply 23 and is applied to grid 26 of x-ray tube 16 through inverting amplifier 80. Consequently, an increase in the feedback signal voltage, in response to a rise in the level of x-ray flux received by detector 14, causes the voltage at control grid 26 to become more negative. The intensity of the electron beam within the x-ray tube 16 then decreases to reduce x-ray production at origin point 17. This maintains the average level of x-ray flux received by detector 14 substantially constant although the scan is now passing through a region of the subject of greater x-ray transmissivity.

Similarly, a decrease in the feedback signal voltage at terminal 99 in response to a decrease of the average level of radiation flux intercepted by detector 14 from passage of the scan through a region of lesser x-ray transmissivity causes the control grid 26 to become more positive. Electron beam intensity and therefore x-ray production at origin point 17 is increased. The average level of radiation flux reaching detector 14 is again maintained substantially constant.

Thus the effect of the feedback circuit 68, when integrating means 71 is adjusted to have a relatively short time constant, is to suppress changes of the detector signal level at terminal 47 other than changes which occur in a brief time period selectable by adjustment of resistor 74 or capacitor 75 or both. The feedback circuit 68 then functions as a spatial frequency filter which suppresses detector signal voltage fluctuations indicative of low spatial frequency variations in the subject 13.

With the feedback circuit 68 adjusted to suppress sustained variations of the detector signal from terminal 47 as described above, the image at first display means 52 exhibits edge enhancement. Boundaries between regions of differing radiopacity within the subject are clearly apparent in the image without being obscured by large differences of contrast between different broad regions of the image. As it is the abruptness of a change of transmissivity between two regions within the subject 13 that varies the detector signal rather than the magnitude of the change in transmissivities, slight changes of transmissivity in the subject which might not be detectable in an ordinary high contrast radiograph are made apparent in the image at first display means 52.

At the same time that the feedback circuit 68 and the first display means 52 are utilized in the manner described above, it is often also desirable to generate a full contrast range image at the second display means 53 and also additional images of selected limited contrast range at the further display means 54 and 55. The information needed to generate such imates has become unavailable from the signals at the detector output terminal 47 as the image at the first display means 52 is now being obtained by suppressing from the detector signals a portion of the information about transmissivity changes in the subject 13 that would otherwise be detected by detector 14. In many instances the low spatial frequency information suppressed by feedback circuit 68 may constitute a very large proportion of the information needed to generate full contrast range images or selected contrast band images.

The second image signal circuit 93 makes it possible to recover the suppressed information and to display images at second, third and fourth display means 53, 54 and 55 derived from all or any selected portion of the total range of information developed by the scanning of the subject 13. In particular, the low spatial frequency information which is being suppressed by the feedback circuit 68 is present in the feedback signal itself at terminal 99. The unsuppressed or high spatial frequency content of the detector signal is available at first image signal terminal 92. Summing amplifier 97 of the second image signal circuit combines the feedback signals from terminal 99 with the first image signals from terminal 92 to produce, at terminal 94, the second image signals containing the full range of spatial frequency information which is realizable from the scanning of the subject 13. Each of display means 53, 54 and 55 receive intensity signals directly or indirectly from terminal 94. Accordingly, simultaneously with operation of the first display means 52, to provide edge enhancement in the image, any or all of the second, third and fourth display means 53, 54 and 55 may be operated in the manner previously described to present full contrast range images and images emphasizing any selected portion or band of the full contrast range.

In some usages of the scanning x-ray apparatus 12, it may be desired to produce an image at first display means 52 indicative of only the low spatial frequency portion of the information realizable from the scanning of the subject 13 or to emphasize a selected range or band of spatial frequencies in the image. By setting switch 79 of the first image signal circuit 78 so that signals from amplifier 82 pass through the second signal integrating or averaging means 86, either of these modes of operation may be realized. In contrast to the first integrating means 71 of the feedback circuit 68, the second integrating means 86 functions effectively as a high spatial frequency filter. Incoming voltage changes from detector signal terminal 47 which are of brief duration are suppressed from the input of amplifier 84 as the voltage on capacitor 88 does not change significantly in response to a brief incoming voltage change but does change gradually in response to a sustained change of input voltage. The range of high spatial frequency voltage changes which is suppressed from the first image signal at terminal 92 is selectable by adjustment of variable resistor 87 or capacitor 88 or both to change the time constant of the first signal integrating means 86.

Accordingly, if the feedback circuit 68 is effectively inactivated by adjusting resistor 74 or capacitor 75 or both to establish a very long time constant at the first integrating means 71 while switch 79 and integrating means 86 of the first image signal circuit 78 are adjusted to suppress brief signal fluctuations from first image signal terminal 92, then first display means 52 exhibits an image emphasizing low spatial frequency changes in the subject or, in other words, changes which are gradual or sustained throughout a broad region within the subject 13.

Alternately, a spatial frequency band pass filtering effect may be produced, to provide an image at first display means 52 emphasizing only a selected middle range of spatial frequency information, by activation of both the feedback circuit 68 and integrating means 86 of the first image signal circuit 78. In particular, integrating means 71 of the feedback circuit 68 may be adjusted to suppress all spatial frequency information from the detector signal at terminal 47 that is below a selected frequency limit while integrating means 86 of the first image signal circuit 78 is adjusted to suppress from terminal 92 all voltage changes indicative of spatial frequencies above a second selected limit. Provided that the second selected spatial frequency limit is higher than the first selected spatial frequency limit, a band pass effect occurs in that only signal changes indicative of spatial frequency information within a selected band of or range of spatial frequencies is transmitted on to the first display means 52.

While the support linkage 111 enables movement of the x-ray apparatus 12 relative to subject 13 to select the region to be imaged, it is possible to arrange for a variety of different views simply by adjusting the raster controls of the x-ray tube 16. Adjustment of the amplitude controls of sweep frequency generators 37 and 41 enables variation of the size of the raster in both the X and Y directions. Variable resistors 38, 39, 42 and 43 enable shifting of the location of the raster on primary anode plate 18. As magnification in the images is determined by the size of the raster, a wide angle or panoramic image of teeth 13 may be produced for initial study. The raster area may then be reduced and relocated on anode plate 18 to produce more magnified and detailed images of individual teeth or limited areas of a tooth that require study. The images appearing on the screens 58 of the display means 52 to 55 are controlled by the same raster or sweep signals that control the location and size of the raster at the x-ray tube 16. Thus, the above described reductions and relocations of the raster area at the x-ray tube 16 also occur at the screens 58 of the display means. Consequently, it is possible to make a series of exposures of different selected areas of the subject 13, such as exposures of different teeth and, because the display means 52 to 55 retain images, the successive views will be retained at different locations on the screens 58 of the display means.

Other aspects, objects and advantages of this invention can be obtained from a study of the drawings, disclosure and the appended claims.

I claim:

1. A signal processing system for scanning x-ray apparatus which has an x-ray source producing a moving x-ray origin point and which has at least one x-ray detector for disposition at the opposite side of a subject to be scanned to produce detector signals from which radiographic images may be derived, the system including feedback circuit means coupled between said detector and said source for generating a feedback signal which regulates said source to maintain the average value of said detector signals substantially constant while enabling brief variations of said detector signals in response to scanning across boundaries between regions of said subject which have different x-ray transmissivities, the system further including a first image signal circuit for producing first image signals in response to variations of said detector signals, wherein the improvement comprises:

a second image signal circuit for producing second image signals containing a greater range of contrast information than said first image signals, said second image signal circuit having signal combining means for combining said feedback signals and said first image signals to produce said second image signals.

2. The apparatus of claim 1 further comprising at least one third image signal circuit having means for selecting and transmitting only a predetermined limited portion of the total range of signal variations present in said second image signals.

3. The apparatus of claim 1 further including a plurality of third image signal circuits each having means for receiving said second image signals and for transmitting a different portion of the total range of signal variations present in said second image signals.

4. The apparatus of claim 3 wherein each of said third image signal circuits includes means for amplifying the portion of said total range of signal variations which is selected by that particular one of said third additional image signal circuits.

5. The apparatus of claim 1 further including first and second display means coupled to said first and second image signal circuits respectively for simultaneously displaying different visible radiographic images of the scanned region of said subject.

6. The apparatus of claim 5 further including at least one third image circuit receiving said second image signals and having means for selecting and transmitting only a limited portion of the total range of variations of said second image signals, and at least one third display means for receiving said third image signals and for displaying a still different visible radiographic image of said subject in response to the same scanning thereof.

7. The apparatus of claim 5 further including data storage means for receiving and storing sets of said first image signals and sets of said feedback signals and for subsequently transmitting at least one of said stored sets of signals to at least one of said display means.

8. Apparatus as defined in claim 7 wherein said data storage means further includes control means for enabling transmission of a selected one of said sets of stored signals to said second image signal circuit and further enabling selective simultaneous transmission of both of said sets of stored signals to said second image signal circuit.

9. The apparatus of claim 7 wherein said system includes at least one third image signal circuit having means for selecting and transmitting only a limited portion of the total range of signal variations present in received signals and wherein said storage means includes means for combining said stored sets of first image signals and feedback signals and for selectively transmitting said combined signals to said third image signal circuit.

10. The apparatus of claim 1 wherein said feedback circuit includes first signal integrating means having a selectable time constant and wherein said first image signal circuit includes second signal integrating means also having a selectable time constant, and wherein said second image signal circuit includes differential amplifier means for algebraically summing said feedback signals and said first image signals to produce said second image signals.

11. In a signal processing system for scanning x-ray apparatus which has an x-ray source in which an x-ray origin point may be scanned in a raster pattern by deflection sweep signals and having at least one x-ray detector for positioning at the opposite side of a region of a subject which is to be imaged and which produces electrical detector signals indicative of x-rays intercepted by said detector after passage through said region of said subject, the combination comprising:

a plurality of display means for generating visible images in response to sweep signals and image intensity signals, a feedback circuit coupled between said detector and said x-ray source and having first signal integrating means for producing a feedback signal which regulates the x-ray output of said x-ray source to maintain the average value of said detector signals substantially constant while enabling brief variations of said detector signals of less than a predetermined duration as determined by the time constant of said integrating means, a first image signal circuit coupled between said detector and a first of said display means and having means for supplying a first image intensity signal thereto which is indicative of said brief variations of said detector signal, and a second image signal circuit having one input coupled to said feedback circuit and another input coupled to said first image signal circuit and having an output coupled to a second of said display means to supply a second image intensity signal thereto, said second image signal circuit having signal summing means for combining said feedback signal and said first image intensity signal to generate said second image intensity signal.

12. The apparatus of claim 11 wherein said first image signal circuit has second signal integrating means for suppressing detector signal variations which are of less than a preselected duration as determined by the time constant of said second signal integrating means, and further includes switch means for selectively actuating and deactuating said second integrating means in said first image signal circuit.

13. The apparatus of claim 11 further comprising at least one third image signal circuit coupled between said second image signal circuit and an additional one of said display means, at least one of said third image signal circuits having amplifier means for transmitting to said additional display means only a selected limited portion of the full range of variations of said second image intensity signal.

14. The apparatus of claim 11 wherein said sweep signals include an X sweep frequency signal for sweeping said x-ray origin point in a first direction and a Y sweep frequency signal for sweeping said origin point in a direction normal to said first direction, said signal processing system further including means for supplying said X sweep frequency signal to the X sweep frequency terminal of one of said display means while supplying said first image intensity signal to the Y sweep frequency terminal of said one of said display means.

15. The apparatus of claim 14 further including means for supplying said Y sweep frequency signal to the Y sweep frequency terminal of a separate one of said display means while supplying said first image intensity signal to the X sweep frequency terminal of said separate one of display means.

* * * * *